(12) United States Patent
Franano

(10) Patent No.: US 8,337,836 B2
(45) Date of Patent: Dec. 25, 2012

(54) METHODS FOR THE TREATMENT AND PREVENTION OF DISEASES OF BIOLOGICAL CONDUITS

(75) Inventor: F. Nicholas Franano, Kansas City, MO (US)

(73) Assignee: Proteon Therapeutics, Inc., Kansas City, MO (US)

( * ) Notice: Subject to any disclaimer, the term of this patent is extended or adjusted under 35 U.S.C. 154(b) by 123 days.

(21) Appl. No.: 12/764,728

(22) Filed: Apr. 21, 2010

(65) Prior Publication Data

US 2010/0203034 A1 Aug. 12, 2010

Related U.S. Application Data

(63) Continuation of application No. 10/546,523, filed as application No. PCT/US2004/005192 on Feb. 20, 2004, now abandoned.

(60) Provisional application No. 60/449,086, filed on Feb. 20, 2003.

(51) Int. Cl.
*A61K 38/48* (2006.01)
*C12N 9/66* (2006.01)
*C12N 9/50* (2006.01)

(52) U.S. Cl. .................. 424/94.64; 424/94.67; 435/218; 435/219

(58) Field of Classification Search ............... 424/94.64, 424/94.67; 435/218, 219
See application file for complete search history.

(56) References Cited

U.S. PATENT DOCUMENTS

| | | | |
|---|---|---|---|
| 5,712,247 A | 1/1998 | Wu et al. | |
| 6,494,861 B1 | 12/2002 | Tsukernik | |
| 7,063,838 B1 | 6/2006 | Franano | |
| 7,153,505 B2 | 12/2006 | Franano | |
| 7,361,335 B2 | 4/2008 | Franano | |
| 7,632,494 B2 | 12/2009 | Franano | |
| 7,883,699 B2 | 2/2011 | Franano | |

FOREIGN PATENT DOCUMENTS

WO  WO 01/21574 A1  3/2001

OTHER PUBLICATIONS

Salacinski et al., "Thermo-mechanical analysis of a compliant poly(carbonate-urea)urethane after exposure to hydrolytic, oxidative, peroxidative and biological solutions," Biomaterials 23:2231-2240, 2002.*
Akimoto, "The effect of pancreatopeptidase E 9elastase) on anastomotic intimal thickness in two types of vascular prosthesis", Surg. Today 25:1027-1033, 1995.
Office Action dated Oct. 21, 2009 in conncection with U.S. Appl. No. 10/546,523.
Chernoyarova et al., "Mechanism of action of active elastase on pancreatic tissue", Bulletin of Experimental Biology and Medicine 78(5):1340-1342, 1974.
Dorbin et al., "Failure of elastin or collagen as possible critical connective tissue alterations underlying aneurismal dilatation", Cardiovasc. Surg. 2(4):484-488, 1994.
International Union of Biochemistry and Molecular Biology (IUBMB). Enzyme nomenclature online, record for pancreatic elastase, EC 3.4.21.36, http://www.chem.qmul.ac.uk/iubmb/enzyme/EC3/4/21/36.html, printed Sep. 21, 2009.
Trubel et al., "Compliance mismatch and formation of distal anastomotic intimal hyperplasia in externally stiffened and lumen-adapted venous grafts", Eur. J. Vasc. Endovasc. Surg. 10(4):415-423, 1995.

* cited by examiner

*Primary Examiner* — Rosanne Kosson
(74) *Attorney, Agent, or Firm* — Dechert LLP

(57) ABSTRACT

Methods are described for dilating biological conduits by removing elastin and remodeling collagens in the wall of the conduit. Methods include the use of agents that increase the release of endogenous elastase and collagenase in the wall of the conduit, either by cells that are normally present in the wall of the conduit or by inflammatory cells that are attracted to the conduit, thereby providing additional conduit dilation. Methods also include the use of agents that increase conduit wall permeability and expose elastin and collagen fibers. Methods also include removing components of the extracellular matrix of arteries and veins leading to an inhibition of intimal hyperplasia in the wall of the vessels by decreasing biomechanical stimuli directed toward the cells in the wall of the vessel. Methods further include the use of agent that degrade microfibers, in addition to elastin, in order to decrease the resynthesis of elastin. Methods also include the use of agent that stabilize the diameter of aneurysmal arteries by blocking cell surface receptors in the wall of the aneurysmal artery that are important in the recruitment of inflammatory cells.

19 Claims, No Drawings

METHODS FOR THE TREATMENT AND PREVENTION OF DISEASES OF BIOLOGICAL CONDUITS

CROSS REFERENCE TO RELATED APPLICATIONS

This application is a continuation of and claims the benefit of U.S. patent application Ser. No. 10/546,523 filed Oct. 2, 2006, which is a National Stage of PCT/US04/005192 filed Feb. 20, 2004, which claims the benefit under 35 U.S.C. §119(e) of U.S. Provisional Application No. 60/449,086, filed Feb. 20, 2003, which is incorporated by reference herein in its entirety.

1. FIELD OF THE INVENTION

The present invention relates to methods for treating or preventing disease in biological conduits. The present invention further relates to methods for delivering therapeutic and prophylactic agents to biological conduits. In certain embodiments, the methods described herein relate to achieving dilation of blood vessels by directly or indirectly degrading elastin and/or remodeling the collagen matrix blood vessel walls. In other embodiments, the methods described herein relate to reducing abnormal dilation of blood vessels by reducing inflammation in the vessel wall.

2. BACKGROUND OF THE INVENTION

2.1. Blood Vessel Structure

A blood vessel is composed of three distinct layers. From inside to outside, these layers include the intima, the media and the adventitia. The intima is a single layer of flat cells that collectively line the lumen. The media is a thick middle layer composed of smooth muscle cells. The adventitia is an outer layer that comprises fibrous covering. Blood flow through arteries and veins is highly sensitive to changes in luminal diameter. Although flow can be increased by the relaxation of the smooth muscle cells of a vessel wall, this result is usually temporary and limited in degree. A large, permanent increase in the luminal diameter of vessels requires degradation and remodeling of the extracellular matrix. This matrix is organized around a weave of two protein fibers, elastin and collagen. The elastin fiber is an inert, insoluble, material that can be extended to nearly twice its initial length and still recoil completely. Under normal hemodynamic conditions, elastin fibers are taut and exert a retractive force on the wall of the vessel that counters the force of distension created by the pumping of the heart. In contrast to elastin, the collagen framework is relatively rigid, and at normal arterial diameters, collagen fibers are slack and contribute little to wall tension. However, during periods of high pressure, the luminal diameter of vessels will increase until the collagen fibers become stretched. At this point, the collagen fiber network resists further dilation and prevents rupture.

2.2. Blood Vessel Obstruction

Arteries obstructed by atherosclerosis often undergo balloon angioplasty. During this procedure, a high-pressure balloon is inflated in a narrowed segment of artery. The balloon enlarges the lumen, often by tearing the wall and disrupting the network of collagen and elastin fibers. The tearing of the arterial wall is associated with mural thrombus formation, platelet deposition, and subsequent narrowing of the lumen at the treatment site by organizing mural thrombus and proliferating smooth muscle cells. The greatest degree of cellular proliferation is associated with tearing of the internal elastic lamina. Not surprisingly, vessels that are treated successfully with balloon dilatation often demonstrate restenosis at the treatment site on follow-up. Initially, research into restenosis focused on the migration and proliferation of smooth muscle cells toward the lumen and the synthesis of extracellular matrix at the treatment site, a process known as intimal hyperplasia. More recently, restenosis has been correlated with a constrictive remodeling process and not with intimal hyperplasia. The single most important factor that determines whether a treated vessel develops restenosis later is whether the remodeling within the wall of the vessel results in enlargement or constriction of the vessel diameter. In many circumstances, a metallic stent is implanted at the site of obstruction to enlarge the lumen to a maximal diameter and prevent constrictive remodeling. However, the implantation of stents can also cause cellular proliferation and synthesis of extracellular matrix protein, resulting in restenosis.

When large arteries are severely narrowed or completely obstructed, the blocked segment is bypassed, using either autologous vein or synthetic conduits made of materials such as Dacron or polytetrafluoroethylene ("PTFE"). During this procedure, one end of the bypass conduit is sewn to a proximal artery and the other end is sewn to a distal artery, thereby diverting the flow of blood around the obstructed segment. In some cases, the luminal diameter of the available distal arterial anastomotic sites is small at the time of implantation, a finding that is correlated with decreased long-term patency. When adequate autologous vein is not available, a synthetic graft of PTFE or Dacron is often used. After these synthetic grafts are implanted, there is an accelerated buildup of intimal hyperplasia in the outflow vessel at the distal anastomosis which is thought to be due, at least in part, to a mismatch in the compliance properties of the graft (rigid) and the outflow vessel (compliant).

Flow through the outflow vein of hemodialysis grafts and fistulas is also compromised by a small initial artery and vein diameter. In addition, nearly all hemodialysis grafts and fistulas eventually fail, usually due to a buildup of intimal hyperplasia in the wall of the outflow vein, leading to a critical stenosis and subsequent thrombosis. The buildup of this material in the wall of the outflow vein is increased by mismatched compliance properties between the artery and vein, and the synthetic graft and the vein.

Although the dilation of arteries is beneficial in many clinical situations, derangements of this process can occur, leading to aneurysm formation. The aorta is the most common location for aneurysm formation, and excessive dilation of the aorta places a person at a higher risk for vessel rupture, hemorrhage, and death. A histologic analysis of the wall of aneurysmally dilated aortas demonstrates a depletion of elastin and collagen, and a chronic inflammatory infiltrate of monocytes, macrophages, and polymorphonuclear cells. This chronic inflammatory process is associated with thrombus that adheres to the wall of the dilated vessel.

2.3. Compliance Mismatch and Neointimal Hyperplasia

Intimal hyperplasia refers to the proliferation of subintimal smooth muscle cells that migrate through the internal elastic lamina and proliferate and secrete matrix proteins, leading to intimal thickening and intimal hyperplasia. Intimal thickening can also be caused by the sequelae of mural thrombus organization. Progression of intimal hyperplasia at distal endto-side anastomoses remains a key cause of late bypass graft failure (Walden et al., 1980, Arch Surg; 115: 1166-1169; Ecbave et al., 1979, Surgery; 86: 791-798). The concept that compliance mismatch between bypass graft and artery contributes to the development of anastomotic intimal hyperplasia has been reported (Baird and Abbott, 1976, Lancet; 2: 948-950). More recently, the influence of bypass graft diameter on distal anastomotic intimal hyperplasia (DAM) has been demonstrated (Binns et al., 1989, Vasc Surg; 10: 326-337). Grafts with diameters equal to host arteries exhibited lowest DAIH and an inverse correlation between DAIH and flow velocity and local shear rate was reported. Furthermore, a recent study noted the formation and extent of DAIH were significantly higher in the groups with a compliance mismatch between graft and recipient artery in comparison to the iso-compliant groups (Trubel et al., 1995, Eur J Vasc Endovasc Surg; 10: 415-423).

Strategies to reduce compliance mismatch and associated neointimal hyperplasia are critical for the long-term patency of a blood vessel receiving a graft. Synthetic bypass grafts used to divert blood around a site of obstruction, unlike autologous or heterologous material used for anastomotic procedures, are less compliant than non-synthetic bypass grafts. A compliance mismatch between the rigid synthetic graft material and the compliant artery or vein results in increased stress on the outflow artery or vein. Poor compliance is a key factor responsible for reduced performance of synthetic vascular grafts. The mismatch in compliance between the artery or vein and the grafts results in high shear stress and turbulence of the blood flow with local stagnation.

A mismatch in vessel compliance (i.e., the ratio of a change in vessel cross-sectional area to a change in vessel pressure) between the vascular graft and the host vessel is indicated as a culprit in neointimal hyperplasia. In order to decrease the likeliness of short and long term detrimental consequences, including neointimal hyperplasia formation, of grafting blood vessels in surgical procedures, and consequently to improve the overall outcome of patients undergoing such procedures, there is a need for improved strategies to reduce compliance mismatch.

Citation or identification of any reference in Section 2 or in any other section of this application shall not be construed as an admission that such reference is available as prior art to the present invention.

3. SUMMARY OF THE INVENTION

The present invention provides methods of treating or preventing disease in a biological conduit.

In certain aspects, invention provides methods of treating or preventing disease in a biological conduit by increasing the external and/or luminal diameter of the biological conduit. In several embodiments of the disclosed herein, the methods of the invention entail one or more of the following, in any desired combination, (a) administering one or more exogenous elastases to the conduit or to a wall of the conduit; (b) administering one or more exogenous collagenases to the conduit or to a wall of the conduit; (c) increasing the local concentration of one or more endogenous elastases and/or collagenases in the conduit or in a wall of the conduit; (d) inducing inflammation locally in the conduit or in a wall of the conduit; (e) degrading microfibers locally in the conduit or in a wall of the conduit; (f) increasing the local concentration of an endogenous chemotactic factor for monocytes, macrophages, or polymorphonuclear cells in the conduit or in a wall of the conduit; (g) activating macrophages in the conduit or in a wall of the conduit; (h) degrading extracellular matrix in the conduit or in a wall of the conduit; and/or (i) degrading proteoglycans or glycoproteins in the conduit or in a wall of the conduit.

As used herein, the term "endogenous" means produced by the subject being treated in accordance with the methods of the invention. As used herein, the term "exogenous" means produced by a source other than the subject being treated in accordance with the methods of the invention.

In certain specific embodiments, a single agent is utilized that can achieve one or more effects enumerated in (a)-(i) above. For example, the methods may comprise the administration of a matrix metalloprotease (the term "matrix metalloprotease" being used interchangeably herein with "matrix metalloproteinase") that displays elastase activity to the conduit, wherein the matrix metalloprotease is administered in an amount that also capable of degrading extracellular matrix in the conduit. In other embodiments, combination therapy entailing the administration of one or more agents may be used to achieve one or more of the effects enumerate in (a)-(i) above.

Exemplary agents that may achieve one or more effects include, for example, matrix metalloproteinase-1, whose substrates include native collagen types III, I, II, VII, X, aggrecan, link protein, entactin, tenascin, and perlecan; matrix metalloproteinase-6, whose substrates include native collagen types I, II, III, VII, X, aggrecan, entactin, and tenascin matrix metalloproteinase-13, whose substrates include native collagen types II, III, I, VII, X, aggrecan, entactin, and tenascin; matrix metalloproteinase-18, whose substrates include native collagen types I, II, and III; matrix metalloproteinase-14, whose substrates include native collagen types I, II, III, aggrecan, fibronectin, and vitronectin; matrix metalloproteinase-16, whose substrates include native type III collagen and fibronectin; matrix metalloproteinase-24, whose substrates include fibronectin and proteoglycans; matrix metalloproteinase-25, whose substrates include native type IV collagen, fibronectin, proteoglycans (DSPG, CSPG), laminin-1, and fibrin/fibrinogen; matrix metalloproteinase-2, whose substrates include elastin, native collagen types I, IV, V, VII, X, XI; matrix metalloproteinase-9, whose substrates include elastin, native collagen types I, IV, V, VII, X, and XI, fibronectin, laminin, aggrecan, link protein and vitronectin.

The methods of the invention that result in increasing the external and/or luminal diameter of a biological conduit preferably do so with a non-transient effect. In various embodiments, the increase in the external and/or luminal diameter of the biological conduit is for a duration of at least 12 hours, more preferably at least 24 hours, and most preferably at least 48 hours. In various embodiments, the increase in the external and/or luminal diameter of the biological conduit is sustained for a duration of at least one week, at least four weeks, at least twelve weeks, at least 6 months or at least one year after the increase is achieved.

In related embodiments, an increase in the external and/or luminal diameter of the biological conduit is achieved during or shortly after the methods of the invention are performed. For example, in certain embodiments, an increase of the external and/or luminal diameter of a conduit being treated by the methods of the invention of at least 5%, more preferably of at least 10%, is achieved during after the first treatment in accordance with the methods described herein or shortly thereafter, for example within no greater than 1 minute, no greater than 5 minutes, no greater than 10 minutes, no greater than 15 minutes, no greater than 30 minutes, no greater than one hour, no greater that 6 hours, no greater than 12 hours, no greater than 24 hours, no greater 3 days, no greater than 5 days or no greater than one week after the first treatment is completed.

In certain aspects, the present invention provides methods of increasing the external and/or luminal diameter of at least a segment of a biological conduit, said methods comprising increasing the local concentration of one or more endogenous elastases or collagenases, wherein said increase is not achieved by administration of an elastase or collagenase, such that the external and/or luminal diameter of said segment is increased, and wherein said increase is sustained for a duration of at least 24 hours after it is achieved, thereby increasing the external and/or luminal diameter of at least a segment of a biological conduit.

In other aspects, the present invention provides methods of increasing the external and/or luminal diameter of at least a segment of a biological conduit, said methods comprising increasing the local concentration of one or more endogenous elastases and/or collagenases and/or administering one or more exogenous elastases and/or collagenases to the conduit or to a wall of the conduit, such that the external and/or luminal diameter of said segment is increased, and wherein said increase is sustained for a duration of at least 24 hours after it is achieved, thereby increasing the external and/or luminal diameter of at least a segment of a biological conduit.

In other aspects, the present invention provides methods of increasing the external and/or luminal diameter of at least a segment of a biological conduit, said methods comprising inducing local inflammation in said segment, such that the external and/or luminal diameter of said segment is increased, and wherein said increase is sustained for a duration of at least 24 hours after it is achieved, thereby increasing the external and/or luminal diameter of at least a segment of a biological conduit.

In yet other aspects, the present invention provides methods of increasing the external and/or luminal diameter of at least a segment of a biological conduit, said methods comprising increasing the local concentration of one or more endogenous elastases and/or collagenases and/or administering one or more exogenous elastases and/or collagenases to the segment or to a wall of the segment and inducing local inflammation in said segment, such that the external and/or luminal diameter of said segment is increased, and wherein said increase is sustained for a duration of at least 24 hours after it is achieved, thereby increasing the external and/or luminal diameter of at least a segment of a biological conduit.

In yet other aspects, the present invention provides methods of increasing the external and/or luminal diameter of at least a segment of a biological conduit, said methods comprising increasing the local concentration of one or more endogenous elastases and/or collagenases and/or administering one or more exogenous elastases and/or collagenases to the segment or to a wall of the segment, and degrading microfibers in the wall of said segment, such that the external and/or luminal diameter of said segment is increased, and wherein said increase is sustained for a duration of at least 24 hours after it is achieved, thereby increasing the external and/or luminal diameter of at least a segment of a biological conduit.

In yet other aspects, the present invention provides methods of increasing the external and/or luminal diameter of at least a segment of a biological conduit, said methods comprising increasing the local concentration of one or more endogenous chemotactic factors for monocytes, macrophages, or polymorphonuclear cells and/or administering one or more exogenous chemotactic factors for monocytes, macrophages, or polymorphonuclear cells to the segment or to a wall of the segment, and activating macrophages locally, for example by increasing the local concentration of one or more endogenous macrophage-activating agents and/or administering one or more exogenous macrophage-activating agents to said segment or to a wall of the segment, such that the external and/or luminal diameter of said segment is increased, and wherein said increase is sustained for a duration of at least 24 hours after it is achieved, thereby increasing the external and/or luminal diameter of at least a segment of a biological conduit.

In yet other aspects, the present invention provides methods of increasing the external and/or luminal diameter of at least a segment of a biological conduit, said methods comprising (i) administering one or more exogenous elastases and/or collagenases to the conduit or to a wall of the conduit and/or increasing the local concentration of one or more endogenous elastases and/or collagenases; (ii) administering one or more exogenous chemotactic factors for monocytes, macrophages, or polymorphonuclear cells to the conduit or to a wall of the conduit and/or increasing the local concentration of one or more chemotactic factors for monocytes, macrophages, or polymorphonuclear cells; and (iii) activating macrophages locally, for example by increasing the local concentration of one or more endogenous macrophage-activating agents and/or administering one or more exogenous macrophage-activating agents to the conduit or to a wall of the conduit, such that the external and/or luminal diameter of said segment is increased, and wherein said increase is sustained for a duration of at least 24 hours after it is achieved, thereby increasing the external and/or luminal diameter of at least a segment of a biological conduit.

In yet other aspects, the present invention provides methods of enhancing the efficacy of an agent in treating a biological conduit, said methods comprising administering to at least a segment of the biological conduit, in a human subject in need thereof, via a parenteral route, a composition comprising said agent, and degrading one or more glycoproteins or proteoglycans in the wall of said segment, such that the permeability of the said wall to said the agent is increased, thereby enhancing the efficacy of the agent in treating the biological conduit. In an exemplary embodiment, an agent that may be used to degrade proteoglycans is trypsin, chymotrypsin, plasmin, or matrix metalloproteinase-15.

In yet other aspects, the present invention provides methods of inhibiting enlargement of at least a segment of a biological conduit, said methods comprising antagonizing a PAR receptor such that enlargement of said biological conduit inhibited, thereby inhibiting enlargement of said biological conduit.

In yet other aspects, the present invention provides methods of reducing or eliminating compliance mismatch between a first blood vessel and a second blood vessel joined by an anastomosis, comprising: administering to a segment in said first blood vessel or in second blood vessel, in a human subject in need thereof, via a parenteral route, a composition comprising one or more elastases or collagenases in an amount effective to inhibit compliance mismatch, thereby reducing or eliminating compliance mismatch between a first blood vessel and a second blood vessel joined by an anastomosis.

In yet other aspects, the present invention provides methods of dilating at least a segment of a biological conduit, said method comprising administering to said segment, in a human subject in need thereof, via a parenteral route, a composition comprising one or more elastases or collagenases in an amount effective to dilate said segment, thereby dilating at least a segment of a biological conduit.

The present invention provides methods for treating an obstructed biological conduit or a conduit susceptible to obstruction, comprising administering to the wall of the conduit an agent leading to the dilation of the conduit. The agent increases the local concentration of one or more elastases or collagenases. In one embodiment, the agent stimulates the synthesis and/or release of elastases and collagenases by cells that normally reside in the vessel wall, in order to facilitate enlargement of the lumen diameter. In another embodiment, a composition is described where one agent is an elastase that is administered in an amount sufficient to persistently increasing the external and/or luminal diameter of the biological conduit and a second agent stimulates the synthesis and/or release of elastases and collagenases by cells that normally reside in the vessel wall. These agents act synergistically, in that the administration of an elastase leads to a dilation of less than 100% and usually less than 50%. The addition of the second agent can lead to dilation in excess of 100%.

Another aspect of the present invention provides methods for treating an obstructed biological conduit or a conduit susceptible to obstruction, comprising administering to the wall of the conduit an agent that induces local inflammation and/or results in the recruitment of monocytes, macrophages, and/or polymorphonuclear (PMN) cells capable of synthesizing and releasing elastases and collagenases in the conduit wall, in order to facilitate the enlargement of the lumen diameter. In some embodiments, the administered agent would be chemotactic for these cells. In one embodiment, one or more of the chemotactic agents comprises of monocyte chemotactic peptide-1, granulocyte macrophage colony stimulating factor, tumour necrosis factor alpha, or an interleukin. Preferably, in a standard in vitro dual chamber assay of chemotactic activity, the agent exhibits at least about 10 percent greater chemotactic activity for monocytes, macrophages, or PMN cells, relative to a control. More preferably, in a standard in vitro assay of chemotactic activity, the agent exhibits at least about 20 percent, more preferably 30 percent, more preferably 40 percent, and even more preferably 50 percent greater chemotactic activity for monocytes, macrophages, or PMNs, relative to a control. In other embodiments, the agent would cause the local synthesis and/or release of endogenous agents that are chemotactic for monocytes, macrophages, or PMNs. One or more of said chemotactic agents comprises monocyte chemotactic peptide-1, granulocyte macrophage colony stimulating factor, tumor necrosis factor alpha, interferon gamma, leukotriene B4, C5a, interleukin-1, or interleukin-8. In another embodiment, a composition is described where one agent is an elastase that is administered in an amount sufficient to persistently increase the external and/or luminal diameter of the biological conduit and a second agent induces local inflammation and/or results in the recruitment of monocytes, macrophages, and/or polymorphonuclear (PMN) cells capable of synthesizing and releasing elastases and collagenases in the conduit wall. These agents are capable of acting synergistically. For example, administration of an elastase leads to a dilation of less than 100% and usually less than 50%, but the administration of the elastase with a second agent as described herein, which when administered alone does not lead to a significant dilation of the conduit, can lead to dilation in excess of 100%.

The present invention provides a method of increasing the external and/or luminal diameter of a biological conduit by administering to the biological conduit a first composition comprising one or more chemotactic factors for monocytes, macrophages, or polymorphonuclear cells and a second composition comprising an agent that is a macrophage-activating agent. In one embodiment, one or more of the chemotactic agents is not an elastase or a collagenase. In another embodiment, the macrophage-activating agent is a bacterial lipopolysaccharide, thioglycollate, or CpG DNA. In a further embodiment, the first and second compositions are the same and/or are administered in synergistic amounts. In a further embodiment, the first composition and second composition are administered concurrently or the first composition is administered prior to the second composition or the second composition is administered prior to the first composition. In an embodiment, the biological conduit is an artery or vein, or an arterial or venous vascular graft. In a further embodiment, a composition is described where one agent is an elastase that is administered in an amount sufficient to persistently increasing the external and/or luminal diameter of the biological conduit and a second agent comprising one or more chemotactic factors for monocytes, macrophages, or polymorphonuclear cells, and a third composition comprising an agent that is a macrophage-activating agent. These agents act synergistically, in that the administration of an elastase leads to a dilation of less than 100% and usually less than 50%. The addition of the second and third agents, which by themselves may not lead to a significant conduit dilation, can lead to a conduit dilation in excess of 100%.

In the present invention, the administered agent can activate one or more members of the G-protein coupled proteinase activated receptor (PAR) family. Four distinct PARs are known, and they have been given the names PAR-1 (thrombin receptor), PAR-2, PAR-3, and PAR-4. PARs are activated when an n-terminal peptide is cleaved from the receptor, revealing a tethered ligand that inserts into the receptor-binding site. PAR receptor activation often leads to tissue inflammation and the recruitment of monocytes, macrophages, and PMNs. In some embodiments, the agent causes increased expression of the endogenous PAR receptor in the target tissue. Preferably, the administered agent is selected from trypsin, trypsin IV, chymotrypsin, mesotrypsin, mast cell tryptase, neutrophil proteinase-1, tissue factor, factor VIIa, factor Xa, thrombin, plasmin, cathepsin G, MCP-1, a PAR-activating peptide, a PAR-activating peptidomimetic, and all members of the family of proteases known as matrix metalloproteinase (Cottrell et al., 2004, J Biol. Chem. Jan. 15, 2004 [Epub ahead of print]). Alternatively, agents that induce expression of endogenous PAR-2 such as TNF-alpha, IL-1 or bacterial Lipopolysaccharide (LPS) are used (Nystedt et al., J. Biol. Chem. 271:14910).

The present invention provides a method of increasing the external and/or luminal diameter of a biological conduit by administering to the biological conduit a first composition comprising an elastase and a second composition comprising an agent that degrades microfibers in the wall of the biological conduit. In one embodiment, the agent degrades one or more fibrillin components of the microfibers. In a further embodiment, the first composition comprising an elastase consists of type I, or type II elastase. In a further embodiment, the first composition comprising an elastase is a pancreatic elastase, macrophage elastase, leukocyte elastase, or a matrix metalloproteinase.

An aspect of the present invention provides a method of enhancing the efficacy of a first agent at a biological conduit by administering to the biological conduit a first composition comprising first agent and a second composition comprising a second agent that degrades one or more glycoproteins or proteoglycans in the wall of the biological conduit in order to increase the permeability of the wall of the biological conduit to the first agent. In one embodiment, the first agent is an elastase or collagenase wherein, the administration is effective to increase the external and/or luminal diameter of the biological conduit. In one embodiment, the first agent is an anti-restenosis agent. In a further embodiment, the first agent is a population of cells wherein, the cells are cardiac myocytes or stem or progenitor cells capable of differentiating into cardiac myocytes, and wherein the first and second compositions are administered percutaneously into the adventitial space. In a further embodiment, the first and second compositions are the same and/or are administered in synergistic amounts. In a further embodiment, the first composition and second composition are administered concurrently or the first composition is administered prior to the second composition or the second composition is administered prior to the first composition. In an embodiment, the biological conduit is an artery or vein, or an arterial or venous vascular graft.

Another aspect of the present invention involves the addition of an agent that degrades microfibers and/or fibrillins to an agent that degrades tropoelastin, for the purpose of decreasing the resynthesis of elastin fibers. Preferably, the administered agent is selected from trypsin, chymotrypsin, and plasmin, and all members of the family of proteases known as matrix metalloproteinases. A reduction in elastin resynthesis may be beneficial in preventing a recovery of elasticity in the vessel wall and thereby an increase in compliance mismatch across an anastomosis.

In some embodiments, the agent is administered directly to a segment of the artery or vein or venous vascular graft. In other embodiments, the agent is delivered into the lumen of the artery or vein, or venous vascular graft. In some embodiments, the agent is applied to the external and/or luminal surface of the artery or vein or the venous vascular graft. In other embodiments, the agent is administered percutaneously into a tissue comprising the biological conduit wherein, the biological conduit is a coronary artery or vein bypass graft connected to a coronary artery. In a further embodiment, the agent is administered percutaneously to the pericardial space.

In some embodiments of the present invention, the agent causes an increase in the endothelial cell surface expression of adhesion molecules or integrins for monocytes, macrophages, and/or PMNs, including intercellular adhesion molecules (ICAMs), vascular cell adhesion molecules (VCAMs), selectins, and/or the beta 2 integrin Mac-1.

Another aspect of the present invention provides methods for treating an obstructed biological conduit or a conduit susceptible to obstruction, comprising administering to the wall of the conduit an agent that degrades proteoglycans, in order to facilitate the delivery of macromolecules, cells, or vehicles for drug delivery (e.g., polymer microspheres) into the wall and/or surrounding tissues. Examples of proteoglycans include, but are not limited to, chondroitin sulfate, keratan sulfate, heparin sulfate, perlecan, versican, syndecan, and serglycin. Preferably, the administered agent is selected from, trypsin, chymotrypsin, and plasmin. Another aspect of the present invention provides methods for treating an obstructed biological conduit or a conduit susceptible to obstruction, comprising administering to the wall of the conduit an agent that degrades proteoglycans and glycoproteins, in order to facilitate the degradation of elastin. Examples of glycoproteins include fibrillin-1, fibrillin-2, laminin, and fibronectin. Examples of proteoglycans are given above. Preferably, the administered agent is selected from trypsin, chymotrypsin, and plasmin, and all members of the family of proteases known as matrix metalloproteinases.

The present invention includes treating an obstructed biological conduit or a conduit susceptible to obstruction, wherein the biological conduit is obstructed or susceptible to obstruction due to compliance mismatch between an artery and vein, an artery and a venous vascular graft, an artery and a synthetic graft, or a vein and a synthetic graft. In an embodiment, the compliance mismatch is between an artery and a vein connected by an anastomosis. In another embodiment, the compliance mismatch is between an artery and a venous graft, or between an artery and a synthetic graft, or between a vein and a synthetic graft, connected by an anastomosis. In an embodiment, the synthetic graft comprises polytetrafluoroethylene (PTFE) or Dacron.

In some embodiments of the present invention, a delivery apparatus such as, for example, a catheter, a syringe, and any other types of delivery apparatus conventionally used can administer the agent. In some embodiments, administration of the agent comprises localizing a delivery apparatus in close proximity to the segment of the biological conduit to be treated. In some embodiments, during delivery of the agent by a delivery apparatus, a portion of the delivery apparatus can be inserted into the wall of the biological conduit. In some embodiments, the lumen of the biological conduit can be pressurized while the agent is delivered to the pressurized segment of the biological conduit. In some embodiments, the lumen of the biological conduit is pressurized by mechanical action. In some embodiments, the lumen of the biological conduit is pressurized with a balloon catheter. In some embodiments, the agent is administered and the pressurizing is performed by the same device. In some embodiments, the agent is administered directly to the biological conduit. In some embodiments, the biological conduit is surgically exposed and the agent is delivered into the lumen or is applied to the external surface of the biological conduit in vivo. In embodiments involving luminal delivery, blood flow through the vessel may be stopped with a clamp to allow the agent to contact the endothelium surface for longer time periods and to prevent inhibition of the agent by serum. In some embodiments, the biological conduit is surgically removed and the agent is delivered to the luminal surface and/or to the external surface of the conduit in vitro. In alternative embodiments, the agent may be delivered through a polymer formulation that is placed as a stent within the vessel to be treated, a clamp or wrap on or around the vessel to be treated, or other device in, around or near the vessel to be treated. In other embodiments, agents are percutaneously injected into a tissue region for purpose of dilating arteries and/or vein within that region. In embodiments aimed at treatment of heart vessels, agents can be delivered through an intravascular catheter, percutaneously delivered to the pericardial space, or directly applied to surgically exposed coronary vessels.

Another aspect of the present invention describes a reduction in the accumulation of intimal hyperplasia within the wall of arteries or vein connected via a surgical anastomosis. This inhibition results from the breakdown of portions of the extracellular matrix of the treated segment resulting in a loss of vessel compliance such that the mismatch in the compliance properties of the vessels connected via the anastomosis is reduced. The degraded matrix components include, but are not limited to elastin, collagen, proteoglycans and glycoproteins. The matrix degradation can be accomplished by applying an exogenous enzyme, or by applying an agent that stimulates the local synthesis and/or release of endogenous enzymes.

One aspect of the present invention includes a method of reducing or eliminating compliance mismatch between a first blood vessel and a second blood vessel joined by an anastomosis by administering to the first or second blood vessel, a composition comprising one or more elastases or collagenases in an amount effective to inhibit compliance mismatch between blood vessels joined by an anastomosis. In one embodiment of the present invention, a method of dilating a biological conduit is presented wherein, a composition is administered comprising one or more elastases or collagenases in an amount effective to dilate the biological conduit.

An aspect of the present invention involves the blockage of PAR receptors and signal transduction pathway(s) to inhibit the enlargement in the diameter of aneurysmally dilated arteries. The administration of a PAR antagonist may block PAR activation of cells that normally reside in the wall of the vessel (including PAR-1, PAR-2, PAR-3, and PAR-4 activation by thrombin, plasmin, and factor Xa (among others). Preferably, the administered agent is selected from either monoclonal antibodies, peptides, peptidomimetic compounds or small molecules (compounds). Alternatively, inhibitors of the PAR signal transduction pathways such as nitric oxide synthase inhibitors, PDGF, TNF-alpha and bFGF receptor antagonists, or MAPK kinase inhibitors can also be administered. Preferably, such agents would be administered orally or by intravenous or intramuscular injection. This PAR receptor blockade may decrease the chronic inflammation present in the wall of aneurysms, decrease the degradation of extracellular matrix proteins, and decrease the death of vascular smooth muscle cells, and slow or stop the dilation of the vessel.

In accordance with the present invention, the biological conduits can include, for example, an artery, vein, an arterial or venous vascular graft, ureter, bronchus, bile duct, or pancreatic duct. Further, the obstruction of the biological conduit can include, for example, a stenosis, stricture, lesion, or occlusion. In certain embodiments, the compositions to be administered are administered to the artery or vein and/or the venous vascular graft and/or arterial vascular graft.

The method of increasing the external and/or luminal diameter of a biological conduit in the present invention includes wherein, the external and/or luminal diameter is increased 5% to 500%. In a further embodiment, the external and/or luminal diameter of a biological conduit is increased by 5% to 25%, by 25% to 50%, by 50% to 100%, by 100% to 200%, by 200% to 400%, or by 400% to 500%. In another embodiment, the external and/or luminal diameter of a biological conduit is increased by 10% to 400%, by 25% to 300%, or by 50% to 200%.

4. DETAILED DESCRIPTION OF THE INVENTION

The present invention provides methods for treating or preventing disease in biological conduits and/or for delivering therapeutic and prophylactic agents to biological conduits.

In some embodiments, the present invention provides methods for enlargement of the external and/or luminal diameters of biological conduits by administration of agents to the biological conduits. In contrast to previous inventions describing conduit enlargement through use of elastases, this invention is, in part, specifically directed towards use of other agents alone or in combination with an elastase to attain increased, more rapid and/or more persistent conduit enlargement than can be attained with an elastase alone. Previous work has shown that use of highly purified pancreatic elastase type I alone to degrade elastin results in a controlled in vivo enlargement of the luminal diameter of arteries by up to about 50%, which allows increased flow of blood through the lumen. However, when highly purified pancreatic elastase type I is combined with an agent that induces inflammation of the wall of the treated blood vessel, degradation of both elastin and collagen occurs and dilation is seen up to 400% in diameter, in a dose dependent manner. The invention also contemplates the use of a single agent, such as matrix metalloproteinase-9, that both degrades elastin and induces inflammation in the wall of the vessel.

Enlargement of the external and/or luminal diameter of biological conduits provides numerous advantages. In one embodiment, the agent(s) are used to prolong the patency of arteriovenous hemodialysis grafts and fistulas in patients with end-stage renal disease. In particular, the agent(s) can be administered into the wall of the inflow artery and/or outflow vein, resulting in an increase in the synthesis of collagenases and elastases by cells that normally reside in the wall, such as endothelial cells, vascular smooth muscle cells, and mast cells. In another embodiment, application of the agent(s) leads to the recruitment of monocytes, macrophages and PMNs to the wall of the conduit. These inflammatory cells can release endogenous elastases and collagenases, and/or stimulate smooth muscle cells or endothelial cells to release elastases and collagenases resulting in greater dilation of the vessels in the days and weeks after the treatment. The enlargement of the lumen counteracts any buildup of intimal hyperplasia at the treatment site. The overall effect of the luminal enlargement is increased flow through larger vessels, and therefore greater long-term patency rates.

In another embodiment, the agent(s) are used to improve long-term patency rates after balloon dilation of biological conduits, including arteries obstructed by atherosclerosis. In particular, the agent can be administered into the wall of a conduit during balloon dilation so as to stimulate the release of elastases and collagenases by cells that normally reside in the vessel wall. The delivered agent can also recruit monocytes, macrophages and PMNs to the wall of the conduit. These inflammatory cells can release endogenous elastases and collagenases, and/or stimulate cells that normally reside in the wall to release elastases and collagenases. The elastases and collagenases then degrade elastin and collagen, resulting in further dilation of the conduit in the days and weeks after the balloon dilation. This delayed luminal enlargement counteracts any buildup of intimal hyperplasia at the treatment site. The overall effect of the use of the agent during balloon dilation is increased flow through a larger lumen, and therefore greater long-term patency rates.

Further, in accordance with the present invention, treatment of the biological conduits with the agents is controlled. It has been found that while the agents are potentially beneficial in certain clinical situations, they can have untoward effects. For example, high doses of porcine pancreatic serine proteases including elastase, trypsin, and chymotrypsin (as well as other unspecified porcine proteins) can lead to severe aneurysmal dilation of arteries, and even rupture. Thus, in accordance with the present invention, the type of agents delivered, the concentration, the method of delivery, and the treatment time are preferably controlled so as to achieve the desired degree of dilation.

Many enzymes cleave elastin and can, therefore, be considered elastases. The selection of a specific enzyme(s) for use as a therapeutic agent is important. Humans synthesize a family of zinc and calcium dependent endopeptidases called matrix metalloproteinases (MMPs) that have the ability to degrade various components of the extracellular matrix, including some that degrade elastin, some that degrade collagen(s) and some that degrade both. Humans synthesize a Type I elastase known as ELA-1, with 89% amino acid homology to Type I porcine pancreatic elastase. Humans also synthesize a Type II and a Type III pancreatic elastase. These elastases are differentiated by their amino acid sequence and substrate specificity. The porcine pancreas produces several elastases, most notably a Type I elastase that rapidly degrades tropoelastin, proteoglycans, and some glycoproteins. Type I porcine pancreatic elastase is not thought to degrade fibrillar collagens or microfibers, and is not thought to activate PAR receptors. Several preparations of porcine pancreatic elastase are available commercially and highly purified preparations are thought to contain Type I elastase almost exclusively. However, the pattern of arterial dilation with these preparations varies with the purity of the sample. Highly purified preparations of pancreatic elastase cause an immediate dilation of the treated artery by about 50%, a finding that correlates with a rapid proteolysis of the elastin matrix. The degree of dilation is unchanged over time. The dilation observed with preparations of pancreatic elastase that are contaminated with other pancreatic serine proteases and pancreatic proteins generally follows a two-step pattern. First, there is approximately a 50% dilation that correlates with a rapid proteolysis of the elastin matrix. This is followed by a progressive dilation of the lumen over the next few days to weeks, which is associated with an inflammation in the wall of the treated segment and an increase in the local concentration of endogenous elastases and collagenases, including MMPs and leukocyte elastase. The inflammation eventually subsides and the vessel diameter stabilizes at around 21 days, leaving a dilated artery that is depleted of elastin. The diameter of an artery can increase as much as 400%, depending on the type and concentration of the enzyme preparation, and the treatment time.

An analysis of the enzymatic activity of the less pure preparations of porcine pancreatic elastase have shown that, in addition to elastase, they contain significant amounts of trypsin and chymotrypsin, two other serine proteases. These trypsin and chymotrypsin contaminants do not, by themselves, cause arterial dilation. However, they have properties that can enhance the dilatory effects of elastase. For example, trypsin stimulates the release of MMPs from vascular smooth muscle cells, possibly through PAR activation. This results in the further degradation of elastin and collagen. In addition, trypsin and chymotrypsin degrade glycoproteins and the core proteins of proteoglycans, which surround elastin fibers in vivo. The removal of glycoproteins and proteoglycans substantially enhances the elastolytic effect of purified elastase in vitro, presumably by removing the glycoproteins and proteoglycans covering the elastin fibers. Also, trypsin and chymotrypsin can permeabilize vessels by removing glycoproteins and proteoglycans from the extracellular matrix of vessels, thereby accelerating the penetration of elastase into the wall of the vessel during treatment. This enhances the diffusion of elastases into the vessel wall during treatment and allows for the convective transfer of agents through the wall.

Furthermore, both trypsin and chymotrypsin degrade microfibers. This small fiber network is laid down during blood vessel development as a "scaffold" on which tropoelastin is inserted. The treatment of lung tissue with highly purified pancreatic elastase and either trypsin or chymotrypsin results in the persistent removal of both tropoelastin and microfibers and a persistent loss of lung elasticity. The combined use of elastase and trypsin on biological conduits described here results in both tropoelastin and microfiber degradation, leading to a persistent loss of conduit elasticity. Adding trypsin reduces the resynthesis of elastin fibers and prevent the return of elasticity. The reduction in vessel elasticity with an elastase and trypsin combination persists longer than the reduction in vessel elasticity with elastase alone. A single enzyme that degrades both tropoelastin and microfibers is a preferable agent for practicing the methods of the present invention relating to increasing the external and/or luminal diameter of biological conduits.

As noted previously, the less purified preparations of porcine pancreatic elastase (containing trypsin) induce an inflammatory response in the treated artery, which results in dilation greater than 50%. Interestingly, trypsin activates PAR-1 and PAR-2, receptors that are present on endothelial cells, vascular smooth muscle cells, and mast cells. Activation of these PARs results in a substantial inflammation and the recruitment of monocytes, macrophages, and PMNs to the treated area. The inflammation seen with activation of the PAR-1 and PAR-2 is thought to result from the synthesis and release of monocyte chemotactic peptide-1 (MCP-1) and other pro-inflammatory cytokines as a result of PAR activation. Increased local concentrations of pro-inflammatory cytokines also stimulate the up regulation of endothelial cell surface receptors, including the ICAMs, VCAMs and selectins, which attract monocytes, macrophages, and PMNs from the circulating blood pool. The infiltration of these inflammatory cells into the wall of a vessel is a key factor in vessel enlargement and allows for vessel dilation greater than 50%. The addition of "activation" agents may be desirable to make pro-inflammatory agents such as MCP-1 effective as vasodilators. These "activation" agents would stimulate monocytes and macrophages leading to a greater release elastases and collagenases when they enter the treated vessel wall (Tambiah et al., 2001, Br. J. Surg. 88(7):935-40; Namiki et al., 2002, Arterioscler. Thromb. Vasc. Biol. 22(1): 115-20; Gunn et al., 1997, J. Immunol. 158(1):376-383). Macrophage stimulating agents such as bacterial lipopolysaccharide (LPS), thioglycollate (e.g., at a concentration of 0.1 mol/l), or CpG DNA are examples of activation agents (Stovall et al., J Biol. Chem. 2004 Jan. 28 [Epub ahead of print; manuscript no. M311434200]). Such agents activate the macrophages that are attracted to the site of treatment and result in an increase in the release of collagenases and elastases (including MMP's) that will result in vessel dilatation.

Furthermore, as a vessel dilates rapidly, the wall thins and the endothelial surface is stretched. PAR activation via trypsin stimulates the synthesis, and release of TNF-alpha, bFGF, and PDGF, which are potent smooth muscle cell and endothelial cell mitogens. The proliferation of smooth muscle cells and endothelial cells in response to the PAR-activator trypsin could be important to reinforce the thinned wall of the treated vessel with cells and matrix, and to cover the enlarged lumen with a confluent sheet of endothelial cells. In certain circumstances, the compliance of the wall of the vessel(s) will be reduced and a compliance mismatch across an anastomosis will be corrected, at least partially. In this setting, the stimulatory biomechanical signals resulting from compliance mismatch will be reduced and intimal hyperplasia will be reduced, when compared to untreated vessel segment(s).

The preferred agent would provide an immediate 50% dilation of the treated vessel, via the removal of elastin, and attract monocytes, macrophages, and PMNs to the treated conduit wall that would act in conjunction with resident smooth muscle cells, endothelial cells, or epithelial cells to cause a secondary dilation of the vessel greater than 50%, through the release of endogenous elastases and collagenases. Such a preparation might be composed of an elastase alone (such as MMP-9), or an elastase with an additive that causes inflammation in the vessel wall. This type of preparation would be particularly useful for dilating hemodialysis graft outflow veins.

Another embodiment of the present invention involves inhibiting the growth of intimal hyperplasia within the wall of a biological conduit by the degrading extracellular matrix components of the treated segment. Degradation of matrix components blocks mitogenic and chemotactic signals from the matrix to the cells responsible for the cell proliferation and extracellular matrix formation that is the hallmark of intimal hyperplasia. Furthermore, degradation of matrix components can lead to apoptosis of vascular smooth muscle cells and fibroblasts and a depletion of the cells that contribute to intimal hyperplasia within the wall of the treated segment. The matrix degradation can be accomplished by applying exogenous elastases and collagenases, or by applying an agent that stimulates the local synthesis and/or release of endogenous elastases or collagenases. The degraded matrix components include, but are not limited to elastin, collagen, glycosaminoglycans, fibronectin, vitronectin, tenascin-C, and laminin.

Another embodiment of the present invention involves the blockage of PAR receptors to slow the dilation of aneurysmally dilated arteries. The administration of a PAR antagonist may block PAR activation by thrombin, plasmin, factor VIIa, factor VIIIa, and factor Xa at the interface between mural thrombus and the vessel wall. This PAR receptor blockade may decrease the chronic inflammation present in the wall of aneurysms and therefore stabilize the numbers of vascular smooth muscle cells and the collagen fibers present, thereby slowing or stopping the dilation of the vessel.

The patients on whom the methods of the invention are practiced include, but are not limited to, animals such as cows, pigs, horses, chickens, cats, dogs, etc., and are preferably mammals, and most preferably human.

The biological conduits that may be treated in accordance with the methods of the invention can include, for example, arteries, veins, ureters, bronchi, bile ducts, or pancreatic ducts.

Where the biological conduit to be treated is obstructed, the obstruction can be, for example, a stenosis, stricture, or lesion.

In practicing the methods of the invention described herein, reference can be made to U.S. application Ser. No. 09/669,051 by Franano, filed Sep. 24, 2000, the entire contents of which are incorporated by reference herein in their entirety.

4.1. Dilating Biological Conduits Using Agents that Increase Local Concentration of Elastase(s) and/or Collagenase(s)

The present invention provides methods for treating an obstructed biological conduit or a conduit susceptible to obstruction, comprising administering to the wall of the conduit an agent leading to the permanent dilation of the conduit. The agent stimulates the synthesis and/or release of elastases and collagenases by cells that normally reside in the vessel wall, in order to facilitate enlargement of the lumen diameter.

4.2. Dilating Biological Conduits by Inducing Inflammation

4.2.1. Chemotactic Agents

Another aspect of the present invention provides methods for treating an obstructed biological conduit or a conduit susceptible to obstruction, comprising administering to the wall of the conduit an agent that results in the recruitment of monocytes, macrophages, and/or polymorphonuclear (PMN) cells capable of synthesizing and releasing elastases and collagenases in the conduit wall, in order to facilitate the enlargement of the lumen diameter. In some embodiments, the administered agent would be chemotactic for these cells. Preferably, in a standard in vitro dual chamber assay of chemotactic activity, the agent exhibits at least about 10 percent greater chemotactic activity for monocytes, macrophages, or PMN cells, relative to a control. More preferably, in a standard in vitro assay of chemotactic activity, the agent exhibits at least about 20 percent, more preferably 30 percent, more preferably 40 percent, and even more preferably 50 percent greater chemotactic activity for monocytes, macrophages, or PMNs, relative to a control.

4.2.2. Inducing the Local Production of Chemotactic Factors

In other embodiments, the agent would cause the local synthesis and/or release of endogenous agents that are chemotactic for monocytes, macrophages, or PMNs. In some embodiments, the administered agent can activate one or more members of the G-protein coupled proteinase activated receptor (PAR) family. Four distinct PARs are known, and they have been given the names PAR-1 (thrombin receptor), PAR-2, PAR-3, and PAR-4. PARs are activated when an n-terminal peptide is cleaved from the receptor, revealing a tethered ligand that inserts into the receptor-binding site. PAR receptor activation often leads to tissue inflammation and the recruitment of monocytes, macrophages, and PMNs. In some embodiments, the agent causes an increase in the endothelial cell surface expression of adhesion molecules for monocytes, macrophages, and/or PMNs, including intercellular adhesion molecules (ICAMs), vascular cell adhesion molecules (VCAMs), and selectins. In other embodiments, the agent causes increased expression of endogenous PAR receptors in the target tissue. Preferably, the administered agent is selected from pancreatic elastase, trypsin, trypsin iv, mesotrypsin1, chymotrypsin, mast cell tryptase, neutrophil proteinase-1, tissue factor, factor VIIa, factor Xa, thrombin, plasmin, cathepsin G, MCP-1, synthetic peptides which activate PARs, peptidomimetic or other small-molecule PAR agonists, macrophage elastase, leukocyte elastase, and all members of the family of proteases known as matrix metalloproteinases (Cottrell et al., 2004, J. Biol. Chem. 2004 Jan. 15 [Epub ahead of print]). Alternatively, agents that induce expression of endogenous PAR-2 such as TNF-alpha, IL-1 or bacterial Lipopolysaccharide (LPS) are used (Nystedt et al., J. Biol. Chem. 271:14910).

4.3. Dilating Biological Conduits By Degrading Microfibrils

Another aspect of the present invention involves the addition of an agent that degrades microfibers and/or fibrillins to an agent that degrades tropoelastin, for the purpose of decreasing the resynthesis of elastin fibers. Preferably, the administered agent is selected from trypsin, chymotrypsin, and plasmin, and all members of the family of proteases known as matrix metalloproteinases. A reduction in elastin resynthesis can be beneficial in preventing a recovery of elasticity in the vessel wall and thereby an increase in compliance mismatch across an anastomosis.

In the present invention, microfiber degrading agents include, but, are not limited to human trypsin, trypsin from other mammals including mouse, rat, pig, cow, horse, human chymotrypsin, chymotrypsin from other mammals including mouse, rat, pig, cow, horse, human plasmin, plasmin from other mammals including mouse, rat, pig, cow, horse, human leukocyte elastase, leukocyte elastase from other mammals including mouse, rat, pig, cow, horse, In various embodiments of the present invention, the microfiber-degrading agent is matrix metalloproteinase-2 (also known as gelatinase A or 72 kd Type N collagenase), matrix metalloproteinase-9 (also known as gelatinase B or 92 kd Type N collagenase), matrix metalloproteinase-7 (also known as matrilysin or PUMP-1), or matrix metalloproteinase-12 (also known as human macrophage elastase or human macrophage metalloelastase). In a preferred embodiment, the matrix metalloproteinase is a human matrix metalloproteinase. In other embodiments, the matrix metalloproteinase is from other mammals such as mouse, rat, pig, cow, or horse.

4.4. Elastase and Collagenase-Based Methods of Dilating Biological Conduits

4.4.1. Collagenases

Collagen is a majority component of the extracellular matrix of multicellular eukaryotic organisms. It is a structural protein which is characterized by regions of small, repeating sequences of amino acids which result in the formation of helical chains between molecules. These helices give rise to its exceptional structural stability and strength. Collagen is the main constituent of the skin, tendons, bones, cartilages and tissues and represents approximately 40% of all the proteins of the human body. Although the collagen molecule is very resistant to the action of most proteases, it can still be degraded by specific proteases referred to as collagenases.

Several members of the enzyme family known as metalloproteinases (MMPs) are collagenases. These enzymes are very widely distributed in the living world and are present, but weakly expressed, in normal physiological situations, such as organ growth and tissue replacement. Their overexpression in man and their activation are related, however, to numerous processes, sometimes pathological processes, which involve the uncontrolled destruction, and the remodelling of extracellular matrix. Two classes of collagenases have been identified and are characterized by the specificity of the cleavage they bring about in the collagen molecule. The first class of collagenases is constituted by collagenases of higher organisms, which hydrolyze the peptide bonds containing Gly--Ile or Gly--Leu, whereas the second class is constituted by bacterial collagenases, which systematically hydrolyze all the peptide bonds having the sequence X--Gly and generally degrade any collagen molecule.

Some enzymes, such as MMP-2, MMP-9, and leukocyte elastase degrade both elastin and some collagens. An agent that degrades elastin rapidly and collagens slowly provides greater dilation than an agent that degrades elastin alone, because of partial collagen degradation and subsequent remodeling after treatment. An agent that degrades collagens but not elastin may be administered directly into the wall of a biological conduit that is obstructed by a collagen-rich tissue, such as intimal hyperplasia, effectively clearing the obstructing material from the lumen of the conduit.

In a preferred embodiment, a collagenase for use in accordance with the present methods and compositions is one that degrades type IV basement membrane collagen.

In alternative embodiments, a collagenase for use in accordance with the present methods and compositions is one that degrades collagens types I, II and III (e.g., matrix metalloprotease types 1, 3, 7, 9 and 10).

In a certain specific embodiment, the collagenase is *Clostridium histolyticum* collagenase.

4.4.2. Elastases

In the methods and compositions of the invention utilizing an elastase, the elastase enzyme employed is preferably a Type I Elastase that preferentially cleaves peptide substrates with small hydrophobic amino acid residues such as alanine. Examples of Type elastases include the human elastase I enzyme (NCBI Accession Number NP_001962) that is expressed in skin and the porcine elastase I enzyme (NCBI Accession Number CAA27670) that is expressed in the pancreas. Alternatively, a Type II Elastase that can cleave peptide substrates with medium to large hydrophobic amino acid residues in the P1 position (i.e., the substrate amino acid residue immediately n-terminal to the scissile bond) may be used. Examples of Type II elastases include the human elastase IIA enzyme (NCBI Accession Number NP254275) and the porcine elastase II enzyme (NCBI Accession Number A26823) that are both expressed in the pancreas.

In the present invention, elastin-degrading agents include, but, are not limited to human pancreatic elastase I (also known as ELA-1), human pancreatic elastase IIA, human pancreatic elastase IIB, human pancreatic elastase IIIA, human pancreatic elastase IIIB, porcine pancreatic elastase I, porcine pancreatic elastase II, porcine pancreatic elastase pancreatic elastases from other mammals, including mouse, rat, cow, horse, human leukocyte elastase, matrix metalloproteinase-2 (also known as gelatinase A or 72 kd Type IV collagenase), matrix metalloproteinase-9 (also known as gelatinase B or 92 kd Type IV collagenase), matrix metalloproteinase-7 (also known as matrilysin or PUMP-1), matrix metalloproteinase-12 (also known as human macrophage elastase or human macrophage metalloelastase), cathepsin L, and cathepsin S. In a preferred embodiment, the elastin-degrading agent is a human elastin-degrading agent. In other embodiments, the elastin-degrading agent is from other mammals such as mouse, rat, pig, cow, or horse.

4.5. Dilating Biological Conduits Using Combination Therapy

Described below are combination methods and related compositions for treating or preventing disease in a biological conduit, for example by enlarging the external and/or luminal diameter of the biological conduit. The methods of the invention involve the administration of at least two agents to a patient, the first of which has diameter-enlarging activity, either directly or indirectly. The second agent is generally capable of enhancing the effect of the first agent, either through facilitating the delivery of the first agent, or through exerting direct (e.g., by degrading elastin) or indirect (e.g., by inducing local inflammation of the conduit) diameter-enlarging activity. In certain embodiments, the combination methods further encompass administering a third agent that is generally capable of enhancing the effect of the first or second agent, either through facilitating the delivery of the first or second agent, or through exerting direct or indirect diameter-enlarging activity.

Accordingly, in certain embodiments, the methods of the invention encompass the combination administration of a combination of any (e.g., two, three, four, five, six or all) of the following types of agents: (1) an elastase; (2) a collagenase; (3) an agent that increases the local concentration of one or more endogenous elastases or collagenases; (4) an agent that induces local inflammation in the segment of the conduit to which it is administered; (5) an agent that degrades microfibers in the wall of the segment of the conduit to which it is administered; (6) a chemotactic factor for monocytes, macrophages, or polymorphonuclear cells; (7) a macrophage-activating agent; and (8) an agent that degrades proteoglycans and/or glycoproteins.

In preferred embodiments of the combination methods disclosed herein, the combination methods comprise the administration of an elastase or a collagenase and at least one of the agents listed in (3)-(8) above that is not an elastase or a collagenase.

In other preferred embodiments of the methods disclosed herein involving the administration of an elastase or collagenase, the elastase or collagenase does not display any one, two, three or four, or all five, of the following activities: (a) increasing the local concentration of one or more endogenous elastases or collagenases; (b) inducing local inflammation; (c) degrading microfibers; (d) increasing the local concentration of an endogenous chemotactic factor for monocytes, macrophages, or polymorphonuclear cells; (e) activating macrophages; (f) degrading extracellular matrix in the conduit; and/or (g) degrading proteoglycans or glycoproteins in the wall of the conduit.

Preferably, where the combination methods comprise the administration of a chemotactic factor for monocytes, macrophages, or polymorphonuclear cells, a macrophage-activating agent is also administered.

Further, the combination methods of the invention encompass performing a combination of any (e.g., two, three, four, five, six or all) of the following methods: (1) an administering an elastase; (2) administering a collagenase; (3) increasing the local concentration of one or more endogenous elastases or collagenases; (4) inducing local inflammation in the segment of the conduit to be treated; (5) degrading microfibers in the wall of the segment of the conduit to be treated; (6) increasing the local concentration of an endogenous or exogenous chemotactic factor for monocytes, macrophages, or polymorphonuclear cells; (7) activating macrophages in the segment of the conduit to be treated; (8) degrading extracellular matrix in the conduit; and/or (9) degrading proteoglycans or glycoproteins in the wall of the conduit.

The combination therapy methods of the present invention often result in a synergistic effect, i.e., a greater than additive effect that would be expected from the agents separately. In some instances, the combination therapy methods of the present invention provide therapeutic benefits where neither agent utilized in combination therapy is effective in isolation. The greater than additive effects can be achieved, for example where the first agent is administered in an amount that is sub-therapeutic. In other instances, the combination therapy methods of the present invention provide benefits greater than the sum of administering each agent alone. For example, with respect to dilation of an external and/or luminal diameter of a biological conduit, the synergistic effect achieved by the administration of two agents can result an external and/or luminal dilation that is at least 5%, at least 10%, at least 20%, at least 30%, at least 50%, or at least 100% greater than the sum of the degree of dilation achieved by administration of either agent alone and, further, in certain specific embodiments, the synergistic effect achieved by the administration of two agents can result an external and/or luminal dilation that is up to 10%, up to 20%, up to 30%, up to 50%, up to 75%, up to 100%, up to 200% or up to 400% greater than the sum of the degree of dilation achieved by administration of either agent alone.

In the present methods, the first agents and second agent can be administered concurrently or successively. As used herein, the agents are said to be administered concurrently if they are administered to the patient on the same day, for example, simultaneously, or 1, 2, 3, 4, 5, 6, 7 or 8 hours apart. In contrast, the agents are said to be administered successively if they are administered to the patient on the different days, for example, the first and second agent can be administered at a 1 day, 2-day or 3-day intervals.

4.6. Treatment or Prevention of Compliance Mismatch

Another aspect of the present invention describes a reduction in the accumulation of intimal hyperplasia within the wall of arteries or vein connected via a surgical anastomosis. This inhibition results from the breakdown of portions of the extracellular matrix of the treated segment resulting in a loss of vessel compliance such that the mismatch in the compliance properties of the vessels connected via the anastomosis is reduced. The degraded matrix components include, but are not limited to elastin, collagen, proteoglycans and glycoproteins. The matrix degradation can be accomplished by applying an exogenous enzyme, or by applying an agent that stimulates the local synthesis and/or release of endogenous enzymes.

4.7. Methods of Inhibiting the Enlargement of Dilated Vessels

A final aspect of the present invention involves the blockage of PAR receptors and signal transduction pathway to slow the enlargement in the diameter of aneurysmally dilated arteries. The administration of a PAR antagonist may block PAR activation of cells that normally reside in the wall of the vessel (including PAR-1, PAR-2, PAR-3, and PAR-4 activation by, for example, thrombin, plasmin, and factor Xa. Preferably, the administered agent is selected from either monoclonal antibodies, peptides, peptidomimetic compounds or small molecules (compounds). Alternatively, inhibitors of the PAR signal transduction pathways such as nitric oxide synthase inhibitors, PDGF receptor antagonists, TNF-alpha receptor antagonists and bFGF receptor antagonists, or MAPK kinase inhibitors can also be administered. Preferably, such agents would be administered orally or by intravenous or intramuscular injection. This PAR receptor blockade decreases the chronic inflammation present in the wall of aneurysms, decreases the degradation of collagen, decreases vascular smooth muscle cell death, and slow or stop the dilation of the vessel.

4.8. Formulations for Delivery of Agents to Walls of Biological Conduits

Another aspect of the present invention provides methods for treating or preventing a disease in a biological conduit by administering to the wall of the conduit an agent that degrades proteoglycans, in order to facilitate the delivery of a therapeutic or prophylactic agent into the wall.

Examples of proteoglycans include, but are not limited to, chondroitin sulfate, keratan sulfate, heparin sulfate, perlecan, versican, syndecan, and serglycin. Preferably, the administered agent is selected from, trypsin, chymotrypsin, and plasmin.

Another aspect of the present invention provides methods for treating or preventing a disease in a biological conduit by administering to the wall of the conduit an agent that degrades proteoglycans and glycoproteins, in order to facilitate the degradation of elastin. Examples of glycoproteins include fibrillin-1, fibrillin-2, laminin, and fibronectin. Examples of proteoglycans are given above.

Preferably, the administered agent is selected from trypsin, chymotrypsin, and plasmin, and all members of the family of proteases known as matrix metalloproteinases.

4.9. Effective Dose

The present invention generally provides the benefit of parenteral, preferably local, administration of agents for treating or preventing disease in biological conduits.

In certain embodiments, as an alternative to parenteral administration, or, where a combination therapy method is utilized, in addition to parenteral administration, oral administration of agents for treating or preventing disease in biological conduits may be used.

Toxicity and therapeutic efficacy of the agents utilized in the practice of the methods of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Such information can be used to more accurately determine useful doses in humans.

In addition to standard methods of elucidating suitable effective doses for practicing the methods of the invention, exemplary methods of elucidating effective doses, for example for synergistic combination therapy, are described in Section 5 below.

4.10. Formulations and Methods of Administration

The invention relates to pharmaceutical compositions and methods of use thereof for preventing or treating disease in biological conduits. Such pharmaceutical compositions can be formulated in a conventional manner using one or more physiologically acceptable carriers or excipients.

In embodiments of the present invention encompassing combination therapy with one or more agents, the one or more agents can be formulated into one pharmaceutical composition, most preferably in amounts that are effective to treat or prevent preventing or treating disease in biological conduits. In alternative embodiments, the one or more agents can be formulated into separate pharmaceutical compositions.

Most preferably, in the compositions of the invention comprising one or more agents useful for practicing the methods of the invention (e.g., one or more of: (1) an elastase; (2) a collagenase; (3) an agent that increases the local concentration of one or more endogenous elastases or collagenases upon its administration to a biological conduit; (4) an agent that induces local inflammation upon its administration to a biological conduit; (5) an agent that degrades microfibers upon its administration to a biological conduit; (6) an agent that increases the local concentration of an endogenous or exogenous chemotactic factor for monocytes, macrophages, or polymorphonuclear cells upon its administration to a biological conduit; (7) an agent that activates macrophages; (8) an agent that degrades extracellular matrix upon its administration to a biological conduit; and/or (9) an agent that degrades proteoglycans or glycoproteins upon its administration to a biological conduit), at least one or more agents are purified to a pharmaceutical grade prior to their formulation into a composition of the invention. In certain specific embodiments, the degree of purity of at least one or more agents prior to such formulation is such that there is no detectable enzymatic activity of any of the other agents suitable for practicing the methods of the invention. Thus, in certain preferred embodiments of the invention, a composition to be administered in accordance with the methods of the invention is prepared by combining a first purified enzyme, e.g., an elastase, in combination with a second purified enzyme, e.g., trypsin.

The agents utilized in the methods of the present invention are generally administered parenterally, often directly to the segment of the biological conduit being treated. Formulations for parenteral administration can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Where oral administration is desired, for example for administering PAR antagonists, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active agent.

The agents of the present invention can be administered to the desired segment of the biological conduit being treated by any device known to one of skill in the art to be cardiovascular delivery, e.g., a syringe, a drug delivery catheter, an implanted drug delivery polymer, such as a sheet or microsphere preparation, an implantable venous catheter, a venous port, a tunneled venous catheter, a chronic infusion line or port, or a polymer-coated vascular stent, preferably a self-expanding stent.

In certain embodiments, the administration to the desired segment may be guided by ultrasound, CT, fluoroscopic guidance, MRI or endoscopic guidance.

In certain aspects of the present invention, administration of an agent to a biological conduit comprises localizing a delivery apparatus in close proximity to the segment of the biological conduit to be treated. In some embodiments, during delivery of the agent by a delivery apparatus, a portion of the delivery apparatus can be inserted into the wall of the biological conduit. In some embodiments, the lumen of the biological conduit can be pressurized while the agent is delivered to the pressurized segment of the biological conduit. In some embodiments, the lumen of the biological conduit is pressurized by mechanical action. In some embodiments, the lumen of the biological conduit is pressurized with a balloon catheter. In some embodiments, the agent is administered and the pressurizing is performed by the same device. In some embodiments, the biological conduit is surgically exposed and the agent is delivered into the lumen or is applied to the external surface of the biological conduit in vivo. In embodiments involving luminal delivery, blood flow through the vessel may be stopped with a clamp to allow the agent to contact the endothelium surface for longer time periods and to prevent inhibition of the agent by serum. In some embodiments, the biological conduit is surgically removed and the agent is delivered to the luminal surface and/or to the external surface of the conduit in vitro.

In other aspects of the present invention, administration of an agent to a biological conduit entails the use of a polymer formulation that is placed as a stent within the vessel to be treated, a clamp or wrap on or around the vessel to be treated, or other device in, around or near the vessel to be treated.

In yet other aspects of the present invention, agents are percutaneously injected into a tissue region for purpose of dilating arteries and/or vein within that region, including collateral arteries. In embodiments aimed at treatment of heart vessels, agents are either percutaneously delivered to the pericardial space or directly applied to surgically exposed coronary vessels.

4.11. Kits

The present invention provides kits for practicing the methods of the present invention. A kit of the invention comprises in one or more containers one or more of the agents described herein as useful for treating or preventing disease in biological conduits, optionally together with any agents that facilitate their delivery, for example a glycoprotein- or proteoglycan-degrading agents.

The kit of the invention may optionally comprise additional components useful for performing the methods of the invention. By way of example, the kit may comprise pharmaceutical carriers useful for formulating the agents of the invention. The kit may also comprise a device or a component of a device for performing the methods of the invention, for example a syringe or needle. In addition or in the alternative, the kits of the invention may provide an instructional material which describes performance of one or more methods of the invention, or a notice in the form prescribed by a governmental agency regulating the manufacture, use or sale of pharmaceuticals or biological products, which notice reflects approval by the agency of manufacture, use or sale for human administration.

5. EXAMPLES

5.1. Example 1

Obtaining Increased Conduit Dilatation Through Recruitment of Monocytes, Macrophages, and Polymorphonuclear Cells to the Conduit Wall Under certain conditions, it is desirable to obtain increases in the lumen diameter of arteries and veins greater than 50%. Methods resulting in appropriate and controlled levels of inflammatory-mediated dilation that yield beneficial outcomes are described here. This example describes how recruitment of activated macrophages to the treated vessel can result in controlled levels of dilation.

To demonstrate the utility of macrophage recruitment in obtaining increased vessel diameter, surgically exposed common carotid arteries (CCA) of a minimum of 4 rabbits are exposed to either: a) pancreatic elastase type I alone (20 U/mL), b) a series of Monocyte Chemoattractant Protein-1 (MCP-1) concentrations ranging from 0.1 to 1000 pg/ml plus bacterial LPS at 10 ug/kg or less i.v. (*Escherichia coli*, Sigma Chemical Co., St. Louis, Mo.) (Parenti et al., 2003, *Am J Physiol Heart Circ Physiol*, December 23 [Epub ahead of print]; Brutzki, 2001, *Hematol J.* 2 (3): 188-195), c) a combination of pancreatic elastase type I (20 U/mL) and MCP-1 concentrations ranging from 0.1 to 1000 pg/ml plus bacterial LPS (as described above) and d) an inert control material (buffer or saline solution). Measurements are made of the artery before, during, and immediately after treatment using a digital camera. At 28 days post-treatment, arterial diameter is determined by angiography with a catheter in the aorta, via a right femoral approach. Sections of the artery are subsequently excised and stained with mouse anti-rabbit macrophage Ab-5, clone RAM11 (Lab Vision, Fremont, Calif.) to quantitate the degree of macrophage infiltration obtained (Tambiah et al., 2001, *Br J. Surg.* 88 (7) 935-940). Both the lumen diameter and macrophage infiltration data are then examined to identify optimized concentrations of MCP-1 for obtaining increased arterial diameter. The surgically exposed CCA of a minimum of 4 animals are then exposed to either: a) pancreatic elastase type I alone b) an optimized Monocyte Chemoattractant Protein-1 (MCP-1) concentration plus bacterial LPS at 10 ug/kg or less i.v. c) a combination of pancreatic elastase type I and the optimum MCP-1 concentration plus bacterial LPS at 10 ug/kg or less i.v. and d) an inert control material (buffer or saline solution). At 28 days post-treatment, arterial lumen diameter is determined by angiography with a catheter in the aorta, via a right femoral approach. The combination of pancreatic elastase type I with an experimentally determined optimal concentration of MCP-1 plus LPS results in an increase in arterial lumen diameter that exceeds that observed for pancreatic elastase type I alone The beneficial effects of treating AV graft outflow veins with pancreatic elastase type I and MCP-1 can also be demonstrated. AV grafts are constructed using the carotid artery and internal jugular vein of pigs by using 4 mm PTFE graft material. The outflow vein is treated with either a) pancreatic elastase type I alone, b) an optimized Monocyte Chemoattractant Protein-1 (MCP-1) concentration plus bacterial LPS at 10 ug/kg or less i.v. c) a combination of pancreatic elastase type I and an optimized MCP-1 concentration plus bacterial LPS at 10 ug/kg or less i.v.) an inert control material (buffer or saline solution), with a minimum of four animals per treatment. High-resolution digital photographs are made of the treated veins before, during, and immediately after treatment using a digital camera. Measurements are made at three locations in the outflow vein by comparison with a standard, and these measurements are averaged. Incisions are closed and the animals are allowed to recover. Follow-up angiography is performed at 28 days, and the vessels are harvested. Sections of the outflow vein are subsequently excised and stained with Mouse Anti-Macrophage Monoclonal Antibody, Clone MAC387 (Abcam Ltd, Cambridge, UK) to quantitate the degree of macrophage infiltration obtained (Tambiah et al., 2001, Br. J. Surg. 88(7):935-40; Namiki et al., 2002, Arterioscler. Thromb. Vasc. Biol. 22(1): 115-20; Flavell et al., 1987, J. Histochem. Cytochem. 35:1217-26). Lumen diameter, wall thickness and intimal hyperplasia are also measured in the treated outflow vein.

5.2. Example 2

Induction of Beneficial Inflammatory Responses in Pancreatic Elastase Type I Treated Conduits via PAR Receptor Activation by Trypsin or Plasmin Under certain conditions, it is desirable to obtain increases in the lumen diameter of arteries and veins greater than 50%. Methods resulting in appropriate and controlled levels of inflammatory-mediated dilation that yield beneficial outcomes are described here. This example describes how activation of the PAR receptor pathway can result in controlled levels of dilation of treated arteries and veins.

This example demonstrates that activators of the PAR receptor must be delivered under carefully controlled conditions and levels to exert the desired effect. In this case, the common carotid artery was surgically exposed in rabbits and treated with either a) 0.9 mg/mL porcine pancreatic elastase type I (Elastin Products Co., Owensville, Mo.) b) 0.9 mg/mL porcine pancreatic elastase type I+0.9 mg/mL chymotrypsin c) 0.9 mg/mL porcine pancreatic elastase type I+0.9 mg/mL trypsin or d) Saline for 30 minutes. Measurements were made before, during, and immediately after treatment using a digital camera. Incisions were closed and the animals were allowed to recover. Follow-up angiography was performed at 42 days, and the vessels were harvested. Significant increases in arterial diameter are observed for vessels treated with porcine pancreatic elastase type I alone. No synergistic increases are observed when either trypsin or chymotrypsin is added at these levels. This is not surprising as the trypsin concentration of approximately 38 uM applied in this instance is approximately 38,000-fold higher than the 1 nM dose needed to evoke a half maximal response when the PAR-2 receptor is expressed in *Xenopus* oocytes (Nystedt et al., 1994, *Proc Natl Acad Sci USA* 91: 9208). The hypothesis that excess trypsin fails to support a stimulatory response is also consistent with the observation excess trypsin can inactivate the PAR-1 receptor (Nakayama et al., 2003, *Br J Pharmacol.* 138 (1) 121-130). It has also been suggested that chymotrypsin and pancreatic elastase type I can inactivate PAR-1 (Altrogge and Monard, 2000, *Anal Biochem*, 277 (1) 33-45). These results point out that both the levels and type of protease used to obtain a desired response must be carefully adjusted. It may also be desirable to stop blood flow through the treated vessel to prevent serum inhibitors from inactivating the PAR-activating agent and provide a sufficient time interval for the PAR-activating agent to cleave PARs located on the vascular endothelium. It may be desirable to use another animal model, such as treatment of the mouse abdominal aorta, as a recent study has shown that Sigma Type I porcine pancreatic elastase does not elicit inflammation in the rabbit carotid artery, as it does in the mouse abdominal aorta.

TABLE 1

Measurements of Artery Diameter (mm)

| Enzyme(s) | 0 min | 15 min | 30 min | 42 min | Contralateral Normal Artery |
|---|---|---|---|---|---|
| Saline Control | 1.8 | 2.1 | 2.2 | 2.3 | 2.4 |
| Elastase | 1.8 | 2.8 | 2.9 | 2.8 | 2.2 |
| Elastase + Chymotrypsin | 1.9 | 2.4 | 2.8 | 3.0 | 2.4 |
| Elastase + Trypsin | 1.7 | 2.9 | 3.1 | 3.0 | 2.4 |

TABLE 2

Changes in Artery Diameter

| Enzyme(s) | Immediate* | 42 days** |
|---|---|---|
| Saline | +21 +/− 2% | −2 +/− 2% |
| Elastase | +65 +/− 8% | +27 +/− 4% |
| Elastase + Chymotrypsin | +52 +/− 10% | +25 +/− 3% |
| Elastase + Trypsin | +89 +/− 14% | +23 +/− 3% |

5.3. Example 3

Procedure for Identifying Conditions for Induction of Beneficial Inflammatory Responses in Pancreatic Elastase Type I Treated Conduits via PAR Receptor Activation To identify appropriate conditions that result in synergistic interactions of pancreatic elastase type I with trypsin or plasmin, mouse abdominal aortas are surgically exposed and surgical clamps are placed on the segment to be treated, to stop the flow of blood through the segment. The clamped segment is then treated with either a) 20 U/mL porcine type I elastase b) 20 U/mL porcine type I elastase+trypsin or plasmin at concentrations ranging from 1 nM to 1 uM trypsin (bovine pancreatic, Sigma Chemical Company, St. Louis, Mo.) or from 0.2 to 5 Units/mL plasmin (Sigma Chemical Company, St. Louis, Mo.) or c) Saline for 30 minutes, with a minimum of four animals per treatment. Measurements are made before, during, and immediately after treatment using a digital camera. Incisions are closed and the animals were allowed to recover. After 28 days, the abdominal aorta is exposed a second time and measurements are made of vessel diameter, and the vessels are harvested.

The beneficial effects of optimized pancreatic elastase type I and trypsin or plasmin application in treatment of an AV graft can also be demonstrated. AV grafts are constructed using the carotid artery and internal jugular vein of pigs by using 4 mm PTFE graft material. The outflow vein is then treated with either a) 20 U/mL pancreatic elastase type I, b) 20 U/mL pancreatic elastase type I+trypsin or plasmin at concentrations ranging from 1 nM to 1 uM, c) trypsin or plasmin alone at concentrations ranging from 1 nM to 1 uM, or d) saline for 30 minutes, with a minimum of four animals per treatment. High-resolution digital photographs are made of the treated vessels before, during, and immediately after treatment using a digital camera. Measurements are made at three locations in the outflow vein using Photoshop, and these measurements are averaged. Incisions are closed and the animals are allowed to recover. Follow-up angiography is performed at 28 days, and the vessels are harvested. Sections of the outflow vein are subsequently excised and stained with Mouse Anti-Macrophage Monoclonal Antibody, Clone MAC387 (Abcam Ltd, Cambridge, UK) to quantitate the degree of macrophage infiltration obtained (Tambiah et al., 2001, Br. J. Surg. 88(7):935-40; Namiki et al., 2002, Arterioscler. Thromb. Vase. Biol. 22(1): 115-20; Flavell et al., 1987, J. Histochem. Cytochem. 35:1217-26). Lumen diameter, wall thickness and intimal hyperplasia are also measured in the treated outflow vein.

5.4. Example 4

Degradation of Proteoglycans to Potentiate Delivery of Pancreatic Elastase Type I, Collagenase, and Other Macromolecules to the Conduit Wall Under certain circumstances, the rate of elastin removal and subsequent vascular dilation is substantially and synergistically accelerated by addition of other proteases such as trypsin or chymotrypsin that degrade proteoglycans that surround and protect the elastin that encases the conduit. In surgical settings, achieving rapid vasodilation can be critical as extended exposure of surgically opened sites is undesirable.

Experiments performed on porcine femoral arteries demonstrate that elastase alone may require extended time periods to exert desirable vasodilatory effects. Superficial porcine femoral arteries were surgically exposed bilaterally, inducing vasospasm. In pilot studies, vessels were treated with highly purified porcine pancreatic elastase type I (PPE; Elastin Products Co., Owensville, Mo.) at 100 U/mL until obvious vasodilation had occurred. Then, four vessels were treated with (100 U/mL) for 60 minutes. Angiography was performed before surgical exposure and after PPE treatment, using a catheter inserted in the distal aorta from a left carotid access.

TABLE

| Angiographic Measurements of Artery Lumen Diameter (mm) | | | |
|---|---|---|---|
| Prior to Exposure | Exposure | Post PPE | % Change (Diameter) |
| 2.9 ± 0.16* | 1.2 ± 0.10** | 4.4 ± 0.48* | 52% |

*average + stdev; n = 4;
**average + range, n = 2

However, when porcine arteries are exposed and subjected to a combination of elastase and proteoglycan degrading enzymes such as trypsin or chymotrypsin, similar degrees of vasodilation are obtained after significantly shorter exposure time intervals. For example, porcine superficial femoral arteries are surgically exposed bilaterally and treated with either a) PPE (100 U/mL) alone b) a combination of PPE (100 U/mL) and trypsin ranging from 0.1 to 1.0 mg/ml c) trypsin at 1.0 mg/ml or d) saline or other inert buffer solutions for up to 60 minutes. Measurements are made before, at 10-minute intervals during, and immediately after treatment using a digital camera to record external arterial diameter. Buffer or trypsin alone treatments do not yield any significant increases in luminal diameter. While elastase alone results in substantial increases in luminal diameter after 60 minutes of exposure, treatment with both elastase and trypsin results in equivalent increases in luminal diameter in significantly less than 60 minutes of exposure time.

5.5. Example 5

Use of PAR Activation Inhibitors to Inhibit Aneurysmal Dilation

Although there is substantial evidence for the involvement of mural thrombus in causing the release of extracellular matrix degrading proteases that cause aneurysms (Fontaine et al., 2002, *Am J Pathol.*, 161 (5) 1701-1710), a direct connection between activation of PAR receptors and induction of aneurysms has not been made. To establish PAR receptors as a viable target for pharmacologically mediated inhibition of aneurysmal dilation, transgenic mice that are genetically deficient for either PAR-1 and/or PAR-2 can be challenged with agents that cause aneurysms (Damiano et al., 1999, *J Pharmacol Exp Ther.*, 228, 671-678) First mating PAR-1–/– mice with PAR-2–/– mice can obtain mice deficient in both PAR-1 and PAR-2. Heterozygous $F_1$ progeny (PAR-1$^{+/-}$ PAR-2$^{+/-}$) are identified by PCR analysis (Wang et al., 2001, *Am J Pathol.*, 159, 1455-1464) and mated. Homozygous $F_2$ progeny (PAR-1$^{-/-}$ PAR-2$^{-/-}$) are identified by PCR analysis and subjected to analyses as follows. In brief, the infra-renal aortic section of PAR deficient and normal control mice are treated with an elastase preparation containing trypsin, chymotrypsin and other protease and non-protein impurities (Type I Porcine Pancreatic Elastase, Sigma Chemical Company, St. Louis, Mo.) to induce formation of abdominal aortic aneurysms (Anidjar et al., 1990, *Circulation*, 32 (3) 973-981). After 1 month, the extent of vessel dilatation and wall thinning is determined first by photographic measurements after surgical exposure and then by histological analysis of pressurized perfusion fixed paraffin imbedded sections of the affected region (Wang et al., 2001, *Am J Pathol.*, 159, 1455-1464). These analyses demonstrate that mice deficient in either PAR-1, PAR-2 or both PAR-1 and PAR-2 display reduced levels of aneurysmal dilatation. It follows from this result that pharmacological blockage of PAR function can also be used to inhibit aneurysm formation.

To directly test various pharmacological inhibitors of PAR for inhibition of aneurysm formation, agents known to inhibit PAR-1 and/or PAR-2 (such as the enzyme thermolysin) is infused into the infra-renal aortic segment of wild-type mice, followed by the infusion of an elastase preparation containing trypsin, chymotrypsin and other protease and non-protein impurities (Type I Porcine Pancreatic Elastase, Sigma Chemical Company, St. Louis, Mo.) to induce formation of abdominal aortic aneurysms (Anidjar et al., 1990, *Circulation*, 82 (3) 973-981). After 1 month, the extent of vessel dilatation and wall thinning is determined first by photographic measurements after surgical exposure, and then by histological analysis of pressurized perfusion fixed paraffin imbedded sections of the affected region (Wang et al., 2001, *Am J Pathol.*, 159, 1455-1464). These analyses are demonstrate that mice pre-treated with PAR-1 and/or PAR-2 inhibitors displays reduced levels of aneurysmal dilatation, when compared with mice treated only with Type I Porcine Pancreatic Elastase (Sigma Chemical Company, St. Louis, Mo.).

6. SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

What is claimed is:

1. A method of reducing compliance mismatch between a first blood vessel and a second blood vessel joined by an anastomosis, comprising:
   administering to a segment in said first blood vessel or in said second blood vessel, in a human subject in need thereof, via a parenteral route, a composition comprising one or more elastases or collagenases in an amount effective to reduce compliance mismatch, thereby reducing compliance mismatch between said first blood vessel and said second blood vessel joined by an anastomosis.

2. The method of claim 1, wherein the one or more elastases or collagenases is in an amount effective to dilate the first blood vessel and said second blood vessel.

3. The method of claim 1, wherein the composition comprises a human elastase.

4. The method of claim 3, wherein the human elastase is human pancreatic elastase I.

5. The method of claim 1, wherein the first blood vessel or second blood vessel is an artery, a vein, an arterial vascular graft, a venous vascular graft or a synthetic graft.

6. The method of claim 1, wherein the compliance mismatch is between an artery and a vein.

7. The method of claim 1, wherein the compliance mismatch is between an artery and a venous graft.

8. The method of claim 1, wherein the compliance mismatch is between an artery and a synthetic graft.

9. The method of claim 1, wherein the compliance mismatch is between a vein and a synthetic graft.

10. The method of claim 8, wherein the synthetic graft comprises polytetrafluoroethylene ("PTFE') or Dacron.

11. The method of claim 9, wherein the synthetic graft comprises PTFE or Dacron.

12. The method claim 1, wherein said composition is directly administered to the first blood vessel.

13. The method of claim 12, wherein said composition is administered by a catheter.

14. The method of claim 13, wherein said composition is administered to a surgically exposed segment of the first blood vessel.

15. The method of claim 13, wherein said composition is delivered into the lumen of the first blood vessel.

16. The method of claim 14, wherein said composition is delivered into the lumen of the first blood vessel.

17. The method of claim 13, wherein said composition is applied to the external surface of the first blood vessel.

18. The method of claim 14, wherein said composition is applied to the external surface of the first blood vessel.

19. The method of claim 12, wherein the first blood vessel is an artery.

* * * * *